United States Patent [19]
Glaug et al.

[11] Patent Number: 5,649,914
[45] Date of Patent: Jul. 22, 1997

[54] TOILET TRAINING AID

[75] Inventors: Frank Steven Glaug; Michael Scott Brunner; Faith Eileen Cochrane; Debra Hartley Durrance, all of Appleton; Christopher Peter Olson, Neenah; Robert Joseph Schleinz; Richard Harry Thiessen, both of Appleton, all of Wis.

[73] Assignee: Kimberly-Clark Corporation, Neenah, Wis.

[21] Appl. No.: 362,291

[22] Filed: Dec. 22, 1994

[51] Int. Cl.⁶ .................. A61F 7/00; A61F 13/15
[52] U.S. Cl. .............. 604/361; 604/291; 604/385.1; 607/114
[58] Field of Search .................. 604/291, 368, 604/385.1, 361; 128/885, 886; 607/114

[56] References Cited

U.S. PATENT DOCUMENTS

| Re. 32,026 | 11/1985 | Yamashita et al. | 126/263 |
|---|---|---|---|
| 1,481,208 | 1/1924 | Johnson . | |
| 2,261,473 | 11/1941 | Jennings | 252/379 |
| 2,907,173 | 10/1959 | Robbins | 62/4 |
| 3,175,558 | 3/1965 | Caillouette et al. | 128/403 |
| 3,306,966 | 2/1967 | Matejcek et al. | 264/321 |
| 3,347,237 | 10/1967 | Jones | 128/285 |
| 3,613,687 | 10/1971 | Kennedy | 128/288 |
| 3,661,142 | 5/1972 | Flam | 128/2 H |
| 3,665,920 | 5/1972 | Davis | 128/287 |
| 3,675,654 | 7/1972 | Baker et al. | 128/287 |
| 3,809,096 | 5/1974 | York | 128/403 |
| 3,881,491 | 5/1975 | Whyte | 128/287 |
| 3,976,049 | 8/1976 | Yamashita et al. | 126/263 |
| 3,977,202 | 8/1976 | Forusz et al. | 62/4 |
| 3,980,070 | 9/1976 | Krupa | 126/263 |
| 4,022,211 | 5/1977 | Timmons et al. | 128/287 |
| 4,081,256 | 3/1978 | Donnelly | 62/4 |
| 4,106,001 | 8/1978 | Mahoney | 340/604 |
| 4,295,517 | 10/1981 | Guex et al. | 165/1 |
| 4,340,563 | 7/1982 | Appel et al. | 264/518 |
| 4,405,297 | 9/1983 | Appel et al. | 425/72 S |
| 4,490,147 | 12/1984 | Pierce et al. | 604/378 |
| 4,573,447 | 3/1986 | Thrash et al. | 126/263 |

(List continued on next page.)

FOREIGN PATENT DOCUMENTS

| 0 138 427 | 4/1985 | European Pat. Off. . |
|---|---|---|
| 0293208B1 | 11/1988 | European Pat. Off. . |
| 0 661 031 | 7/1995 | European Pat. Off. . |
| 0 704 195 | 4/1996 | European Pat. Off. . |
| 3 608 114 | 9/1987 | Germany . |
| 2 244 201 | 11/1991 | United Kingdom . |
| 2244201 | 11/1991 | United Kingdom . |
| 2259018 | 3/1993 | United Kingdom . |
| 2 259 018 | 7/1995 | United Kingdom . |
| WO86/04219 | 7/1986 | WIPO . |
| WO90/08524 | 8/1990 | WIPO . |
| WO93/19716 | 10/1993 | WIPO . |
| WO93/23005 | 11/1993 | WIPO . |
| WO93/25177 | 12/1993 | WIPO . |
| 96/06587 | 3/1996 | WIPO . |

OTHER PUBLICATIONS

Perry's Chemical Engineers' Handbook, Sixth Edition; pp. 3-157 through 3-159; 1984; McGraw—Hill, Inc. United States of America.

R. A. Lofquist et al.; "Hydrophilic Nylon for Improved Apparel Comfort" from the Textile Research Journal, vol. 55, No. 6, pp. 325-333; Jun. 1985.

Primary Examiner—John G. Weiss
Assistant Examiner—Dennis Ruhl
Attorney, Agent, or Firm—Thomas M. Gage

[57] ABSTRACT

A toilet training aid is in the form of a pad that creates a noticeable, distinct feeling during urination. In particular embodiments, the pad may provide the wearer with a temperature change sensation, a wet sensation, a dimensional change sensation, or some combination thereof to signal that urination is occurring. The toilet training aids are desirably attached to a garment by a consumer, thus enabling the consumer to select the type of accompanying garment and the particular time that is best suited to toilet training.

18 Claims, 7 Drawing Sheets

U.S. PATENT DOCUMENTS

| | | | |
|---|---|---|---|
| 4,615,695 | 10/1986 | Cooper | 604/385 A |
| 4,639,949 | 2/1987 | Ales et al. | 2/400 |
| 4,640,284 | 2/1987 | Ruderian | 128/399 |
| 4,699,823 | 10/1987 | Kellenberger et al. | 428/219 |
| 4,735,622 | 4/1988 | Acuff et al. | 604/361 |
| 4,773,863 | 9/1988 | Douglas, III | 434/247 |
| 4,778,459 | 10/1988 | Fuisz | 604/378 |
| 4,854,332 | 8/1989 | Hanakura | 131/365 |
| 4,865,597 | 9/1989 | Mason, Jr. et al. | 604/385.1 |
| 4,924,084 | 5/1990 | Lask et al. | 250/227.25 |
| 4,938,753 | 7/1990 | Van Gompel et al. | 604/385.2 |
| 4,938,756 | 7/1990 | Salek | 604/368 |
| 4,940,464 | 7/1990 | Van Gompel et al. | 604/396 |
| 4,987,908 | 1/1991 | Sprinkel et al. | 131/365 |
| 5,043,704 | 8/1991 | Blakeney | 340/573 |
| 5,062,839 | 11/1991 | Anderson | 604/385.1 |
| 5,074,854 | 12/1991 | Davis | 604/385.1 |
| 5,123,411 | 6/1992 | Noziri | 128/403 |
| 5,147,343 | 9/1992 | Kellenberger | 604/368 |
| 5,147,345 | 9/1992 | Young et al. | 604/378 |
| 5,167,655 | 12/1992 | McCoy | 604/396 |
| 5,170,781 | 12/1992 | Loomis | 128/118.1 |
| 5,178,139 | 1/1993 | Angelillo et al. | 604/385.1 |
| 5,192,606 | 3/1993 | Proxmire et al. | 428/284 |
| 5,197,958 | 3/1993 | Howell | 604/361 |
| 5,217,447 | 6/1993 | Gagnon | 604/397 |
| 5,266,592 | 11/1993 | Grub et al. | 514/452 |
| 5,277,180 | 1/1994 | Angelillo et al. | 607/114 |
| 5,342,343 | 8/1994 | Kitaoka et al. | 604/385.2 |
| 5,348,750 | 9/1994 | Greenberg | 426/3 |
| 5,520,674 | 5/1996 | Lavon et al. | 604/385.1 |

{5,649,914}

TOILET TRAINING AID

BACKGROUND OF THE INVENTION

The present invention relates to articles for assisting children through the toilet training process. More particularly, the invention pertains to a pad that can be positioned in a child's garment at selected times to enhance the toilet training process by providing an indication of when urination occurs to the child.

In recent years, the use of disposable absorbent training pants has become increasingly important in the toilet training process. Disposable training pants represent an intermediate stage for a child between diapers and underpants. Training pants are three-dimensional articles like underpants, yet provide an absorbent function like diapers.

While the aim of the toilet training process is for the child to independently use the toilet, an initial step is for the child to recognize when urination occurs. Recognition can represent a substantial hurdle in the training process, because urination may occur during an activity that may by itself distract the child's attention. Additionally, a child's ability to recognize when urination occurs may be lessened by the improved performance of disposable absorbent products. For example, current disposable training pants and diapers have the ability to quickly draw and retain liquid away from the wearer's skin. As a result, there may be relatively few external signals to the child that urination is occurring. Additionally, current disposable training pants minimize the occasions of leakage and reduce the ability to monitor the toilet training process.

In one attempt to enhance a child's recognition of when urination occurs, training pants have been designed with a bodyside liner material that retains moisture. These so called "wet liners" provide the child with a damp sensation which is thought to be noticeable. Unfortunately, however, disposable training pants that incorporate wet liners may present deficiencies of their own. In particular, consumers are left with the choice of using the product with the wet liner all the time, or maintaining a supply of a second type of training pants that does not incorporate the wet liner. The former option is not satisfactory because some consumers dislike the idea of maintaining a wet sensation in situations where the child is unlikely to vocalize the need for a toilet. The latter option is inconvenient, costly and burdensome for consumers.

Therefore, what is lacking and needed in the art is a toilet training aid that provides an indication of when urination occurs to the child and that can be used with a variety of garments at selected times to maximize the potential for accelerating the toilet training process.

SUMMARY OF THE INVENTION

In response to the discussed deficiencies in the prior art, a new toilet training aid has been developed. Toilet training aids of the present invention create a noticeable, distinct feeling during urination. The toilet training aids are designed to be attached to a garment selected by the consumer. Thus, the consumer can select both the type of accompanying garment and the particular time that is best suited to toilet training. By targeting specific times for toilet training and increasing the likelihood that the child will recognize that urination is occurring, the effectiveness of the toilet training process is enhanced.

In one aspect, the present invention concerns a toilet training aid in the form of a pad including a temperature change member comprising a temperature change substance that provides a possible total energy change of from about 6 to about 30 cal/cm$^2$. The pad also includes attachment means for attaching the pad to a garment.

In another aspect, the present invention concerns a toilet training aid in the form of a pad including a wet sensation layer and attachment means for attaching the pad to a garment. The pad has a relative surface moisture value of at least about 60 percent at approximately 1 minute after a liquid insult, a liquid retention capacity of less than about 6 grams, and a surface area of from about 2 to about 70 square centimeters.

In another aspect, the invention concerns a toilet training aid in the form of a pad including a dimensional change member that is adapted to expand to at least about 2 times its dry height or contract to less than about one-half of its dry height in 10 seconds. The pad, which also includes attachment means for attaching the pad to a garment, is formed of liquid permeable materials such that liquid can pass through the pad.

The particular embodiments of the toilet training aid may provide the wearer with a cool or warm sensation, a wet sensation, an expanding or contracting dimensional change sensation, or some combination of temperature, wet, and dimensional sensations to signal to the child that urination is occurring. The various embodiments of the invention satisfy the unmet need for diverse kinds of training options, which are required because what may work well for one child may not work similarly for another. The invention also concerns a toilet training article that includes a three-dimensional training pant having a crotch region and an inner surface. A toilet training aid in the form of a pad is attached to the inner surface of the training pant in the crotch region.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Within the context of this specification, each term or phrase below will include the following meaning or meanings:

(a) "bonded" refers to the joining, adhering, connecting, attaching, or the like, of two elements. Two elements will be considered to be bonded together when they are bonded directly to one another or indirectly to one another, such as when each is directly bonded to intermediate elements.

(b) "disposed," "disposed on," "disposed with," "disposed at," "disposed near" and variations thereof are intended to mean that one element can be integral with another element, or that one element can be a separate structure bonded to or placed with or placed near another element.

(c) "fabrics" is used to refer to all of the woven, knitted and nonwoven fibrous webs.

(d) "filament" refers to a member having a high ratio of length to diameter or width. Thus, a filament may be a fiber, a thread, a strand, a yarn or any other member or combination of these members.

(e) "liquid impermeable" when used to describe a layer or laminate means that liquid such as urine will not pass-through the layer or laminate under ordinary use conditions in a direction generally perpendicular to the plane of the layer or laminate at the point of liquid contact.

(f) "longitudinal" and "transverse" have their customary meanings, as indicated by transverse section lines 3—3, 6—6, 8—8 and 11—11 respectively in FIGS. 2, 5, 7 and 10.

(g) "member" when used in the singular can have the dual meaning of a single element or a plurality of elements.

(h) "nonwoven web" means a web of material which is formed without the aid of a textile weaving or knitting process.

(i) "releasably attached," "releasably bonded," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the garment.

(j) "two dimensional" refers to a garment that can be opened without destructively tearing any structure while being laid in a flat condition. These garments, such as diapers, do not have continuous leg and waist openings, and require a fastening device, such as adhesive tapes or hook-and-loop fasteners, to attach the garment about the wearer.

(k) "three dimensional" refers to a garment similar to underwear, shorts or pants in that it has continuous leg and waist openings that are bounded by material of which the garment is made. The garment may or may not have manually tearable seams.

These definitions may be defined with additional language in the remaining portion of the specification.

DETAILED DESCRIPTION OF THE PREFERRED EMBODIMENTS

Figure 1:
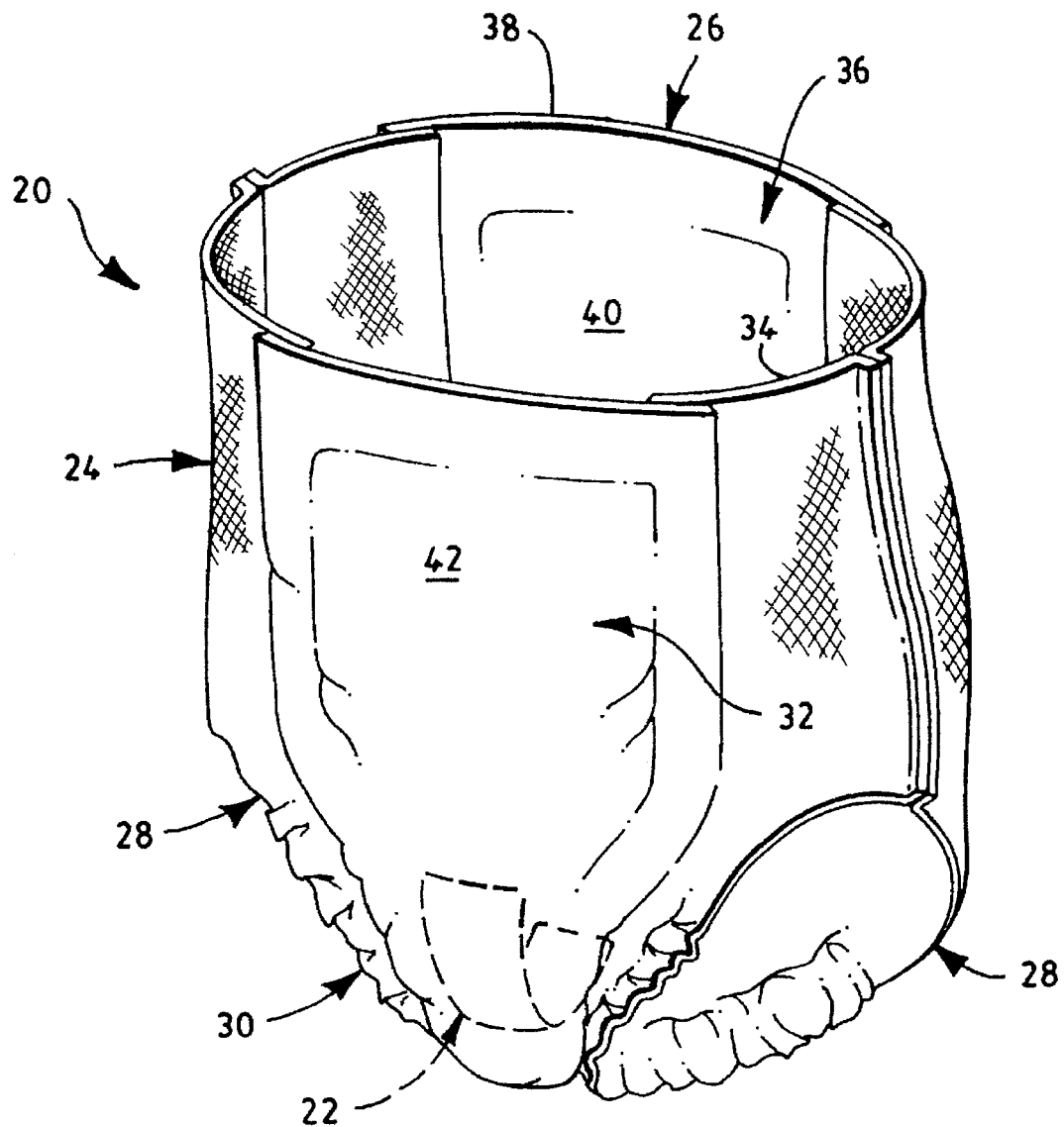
FIG. 1 is a perspective view of a disposable toilet training article according to the present invention, which includes a toilet training aid attached to a training pant.

With reference to FIG. 1, a toilet training article 20 formed according to the invention is shown for purposes of illustration as a toilet training aid 22 attached to the inside of a three-dimensional, disposable, toilet training pant 24. The training aid 22 is designed to create a noticeable, distinct feeling during urination, which should advance the toilet training process by drawing the child's attention to the fact that urination is occurring.

A number of specific embodiments of the training aid 22 are illustrated in FIGS. 2–11. These embodiments provide, either alone or in combination, a temperature change, a retention of moisture, or a dimensional change upon contact with an aqueous solution such as urine. The various embodiments have been developed in recognition of the fact that a given child may respond more positively to some of these training aids 22. With these embodiments, the consumer may select whether a temperature change sensation, a wetness sensation, a dimensional change sensation, or some combination thereof, would work best for the child.

While the toilet training aid 22 is illustrated in FIG. 1 with a disposable training pant 24, the training aid 22 may also be used in conjunction with other garments. For example, a toilet training aid 22 of the invention may be used with underwear, other disposable absorbent garments such as diapers, diaper pants, washable or reusable absorbent garments such as woven training pants, plastic training pants, or the like.

The training aid 22 is desirably attached to the garment by the consumer. This gives the consumer the choice of the type of garment to use with the training aid 22, and the ability to use the training aid without also purchasing one specific type of accompanying garment. Also, the consumer can control when the training aid 22 is used. For instance, the training aid 22 might be effectively used when at home during the daytime. Most desirably, the consumer will select times when the child can benefit most from the enhanced toilet training afforded by the training aid 22. For example, the consumer may realize that enhanced training is not productive during the night, while at special events, or when shopping or in the care of a baby sitter.

Alternatively, however, the training aid 22 can be attached to the garment when the garment is manufactured. In this case, the training aid 22 is desirably releasably attached to the garment so that the consumer still has the option of removing the training aid. For example, the training aid 22 can be releasably attached to the training pant 24 using adhesives, thermal bonds, ultrasonic bonds, hook-and-loop type fasteners, or the like.

The training pant 24 is a three-dimensional garment and thus defines a waist opening 26 and two leg openings 28. A crotch region 30 of the pant 24 is generally located between the leg openings 28 and comprises that portion of the pant which, when worn, is positioned between the legs of the wearer and covers the lower torso of the wearer. A front waist region 32 of the pant 24 extends generally from the crotch region 30 to a front end 34 of the pant, and a back waist region 36 extends from the crotch region 30 to a back end 38 of the pant. The training pant 24 also includes an inner surface 40 and an opposite outer surface 42.

Figure 2:
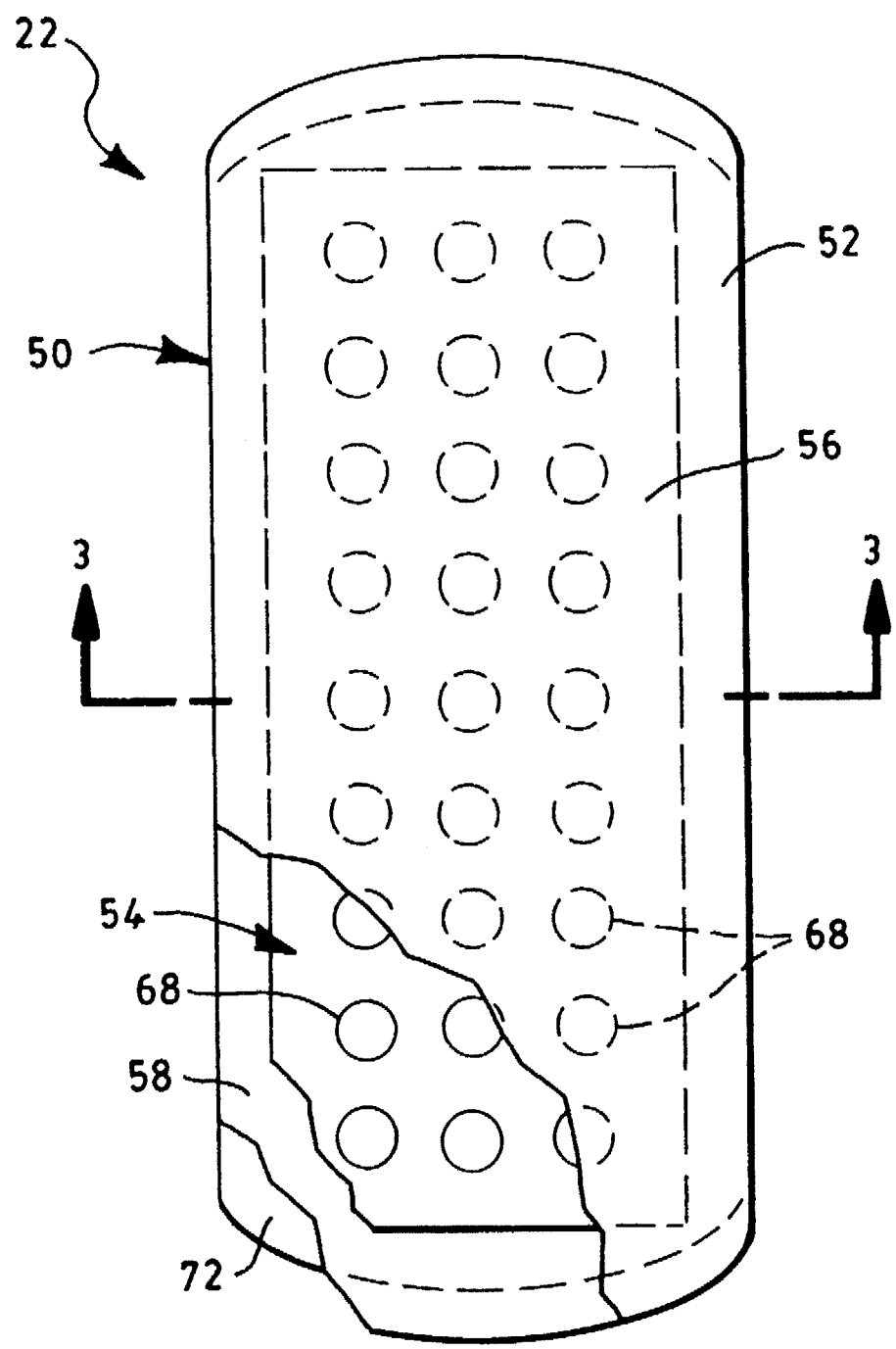
FIG. 2 is a top plan view of the toilet training aid shown in FIG. 1, with portions broken away for purposes of illustration.
Figure 3:
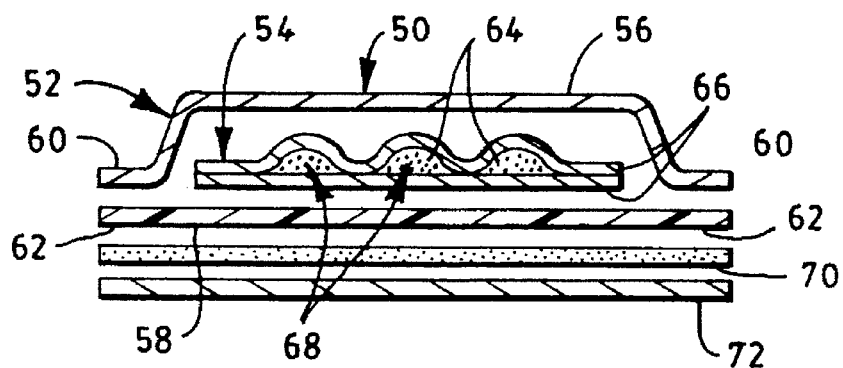
FIG. 3 is a transverse section view taken generally from the plane of the line 3—3 in FIG. 2, but with the components of the toilet training aid separated from one another to better illustrate the invention.

One embodiment of the toilet training aid 22 is illustrated by a pad 50 in FIGS. 2 and 3. Throughout the drawings, the components illustrated in section views such as FIG. 3 are shown separated from one another, although it should be understood that the components actually contact one another. The pad 50 is adapted to be releasably attached to the inner surface 40 of the training pant 24, desirably in the crotch region 30. When the training pant 24 is worn, the pad 50 will be positioned against the skin of the wearer and located so that urine contacts the pad during urination. More desirably, urine is allowed to pass rapidly through the pad 50 during urination. The pad 50 illustrated in FIGS. 2 and 3 is adapted to provide the wearer with a noticeable warm or cool sensation and a noticeable wet sensation, which facilitate recognition by the wearer that urination is occurring.

The pad 50 includes a casing 52, a temperature change member 54, and an attachment means for attaching the pad 50 to a garment, such as the training pant 24. The casing 52 in the illustrated embodiment includes a wet sensation layer 56 and a support layer 58, and the temperature change member 54 is desirably sandwiched within the casing between the wet sensation layer and the support layer. The wet sensation layer 56 and the support layer 58 are desirably longer and wider than the temperature change member 54. In this way, the periphery 60 (FIG. 3) of the wet sensation layer 56 and the periphery 62 (FIG. 3) of the support layer 58 may be bonded directly together by adhesives, thermal bonds, ultrasonic bonds, or other suitable means (not shown).

The wet sensation layer 56 is designed to provide a wet or damp sensation against the skin upon urination, so that the child's attention is drawn to the fact that urination has occurred or is occurring. Wet sensation layers 56 suitable for the present invention desirably cause the training aid 22 to have a relative surface moisture value of at least about 60 percent at approximately 1 minute after a liquid insult, and more particularly at least about 75 percent at approximately 1 minute after a liquid insult for improved performance. A suitable procedure for determining the relative surface moisture value of a training aid 22 is set forth below.

The relative surface moisture in the wet sensation layer 56 and the overall training aid 22 is calculated from measurements made using a Surface Dryness Measuring Equipment apparatus manufactured by Hoechst Atkiengesellschaft of West Germany. A detailed description of this type of equipment and its operation can be found in U.S. Pat. No. 4,924,084 issued May 8, 1984 to Lask et al., which is incorporated herein by reference in its entirety. The equipment for this apparatus includes a Strip chart recorder from the Linear Instrument Corporation of Reno, Nev. (Model 1201). The chart recorder records moisture readings from an optical light sensor which in turn is connected to a DC power source. Prior to the conductance of testing, the equipment is turned on and allowed to warm up for a minimum of 45 minutes.

To prepare a sample for testing, a pad 50 is centered on an absorbent mat. The absorbent mat measures 40.6 by 9.5 centimeters and includes an absorbent structure covered by a liquid permeable liner. The liner is a spunbond polypropylene web having a basis weight of 20 grams per square meter (gsm) and including 0.3 weight percent hydrophilizing surfactant treatment. The absorbent structure includes 16 g of wood pulp fluff and a generally layered arrangement of 12 g of superabsorbent material, and has a density of 0.15 to 0.2 grams per cubic centimeter (g/cc). The absorbent mat is positioned in a leak-proof container. The pad 50 is positioned so that any attachment means bonds the pad to the liner of the absorbent mat.

To test each sample, each sample is placed on top of a plexiglass plate approximately the same size as that of the sample. In order to normalize the moisture values for each sample, a dry reading and a wet reading are both obtained in addition to the actual wetness curve which is generated over a preselected time interval of 10 minutes.

To obtain a dry reading and thus a lower limit on the graph, the sensor is placed over the top of the pad 50 with the longitudinal axis of the sensor being perpendicular to the longitudinal axis of the sample and with the ends of the optical light sensor extending equidistant over both side edges of the sample. The sample is positioned with the pad 50 adjacent the light sensor and the leak-proof container on the plexiglass support. The chart pen is then activated by switching the recorder from stand-by to record and the pen is then zeroed over the 20 grid mark location. The recorder is then returned to stand-by and the detector is removed from the sample.

Next a stainless steel ring having a 6 centimeter inner diameter, a height of 4 centimeters and a weight of approximately 326 grams is centered over the pad 50 in the same location as the previous dry reading. Into the center of the steel ring there is poured 80 milliliters of certified blood bank saline (Catalogue No. B3158-1) from the Baxter Healthcare Corporation, Scientific Products Division, McGraw Park, Ill. The saline solution is a stabilized isotonic 0.9% saline solution containing no preservatives. The saline solution is at ambient temperature (72° to 74° F.) (22° to 23° C.). The 80 milliliters of saline solution is quickly poured into the ring and thus onto the pad 50. Immediately after the saline solution is absorbed below the surface of the pad (no excess liquid standing on the pad), the stainless steel ring is removed and the optical light sensor is immediately placed on top of the sample in the same manner as described before and the chart recorder is switched from stand-by to record. The recorder is adjusted to a chart speed of 1 centimeter per minute and the test is allowed to run for a total of 10 minutes.

At the end of the ten minute interval, the chart pen is lifted and the chart is turned off by switching the chart to stand-by. Next, the ring is placed back on top of the sample in the same location as before and the sample is totally saturated by pouring an additional quantity of saline solution generally in an amount of about 100 milliliters so as to completely saturate the absorbent mat. The amount of liquid in the absorbent mat after the second insult should be enough such that the weight of the sensor causes slight flow back of the liquid to the surface. The ring is then removed and the optical light sensor, whose optical sensing portion is wiped free of any excess saline solution from the previous measurement, is placed in the same location on top of the sample in the same manner as described above. The chart is again switched from stand-by to record and the chart is either momentarily activated or the chart paper is moved back and forth so as to achieve a mark or location on the grid paper representing the total saturation measurement for the sample. Each sample tested then has a zero or dry value ($V_D$), a total saturation value ($V_S$) and a time dependent curve extending from the point of absorption of the initial 80 milliliters of saline solution to a point 10 minutes later.

Following the collection of this data, the relative surface moisture values are calculated using the following equation:

$$\text{relative surface moisture (\%)} = \frac{V_T - V_D}{V_S - V_D} \times 100 = V_R$$

where:

$V_T$ is the value on the curve at a given time.

$V_D$ is the value on the curve when the sample is dry.

$V_S$ is the value on the curve when the sample is saturated.

The wet sensation layer 56 comprises a web of material which is made from a plurality of fibers which can be woven or nonwoven. Suitable webs of material may comprise any type of fiber, such as short staple fibers or longer, more continuous fibers, as are found for example in meltblown and spunbond webs. The fibers may be natural, synthetic or a combination thereof, and may be hydrophilic or hydrophobic by nature or they may be treated to be such. The webs of material may be bonded by methods such as hydroentangling, needling, stitching, heat bonding, adhesive bonding, ultrasonic bonding, through air bonding, point bonding, or the like. The wet sensation layer 56 may be colored, blue or pink for example, to highlight the presence of the pad 50. Suitable wet sensation layer materials are disclosed in U.S. patent application Ser. No. 08/268,967 of Collier et al. filed Jun. 30, 1994 (Attorney Docket No. 11,521), which is incorporated herein by reference.

One suitable material for the wet sensation layer 56 is a spunbond web having a basis weight of at least about 14 gsm (0.4 osy). The fibers are desirably bicomponent fibers which include a water-absorbing component, such as those formed of a material identified under the tradename HYDROFIL and available from Allied Corporation, Fibers Division of Petersburg Va., U.S.A. In one embodiment, the fibers are side-by-side bicomponent fibers comprising 40 volume percent HYDROFIL material and 60 volume percent polypropylene. The fiber denier is desirably less than about 2.0 dpf, and more particularly less than about 1.5 dpf for improved performance. The bicomponent spunbond web can be point-bonded or through-air bonded. A spunbond web of this type does not require additional treatments or additives, such as a wettability treatment.

By way of further illustration, the wet sensation layer 56 may also comprise a polypropylene spunbond web with an added absorbent staple fiber component, such as rayon fibers having a staple length of about 2.5 to about 3.2 cm. (1–1.25 inch), fibrous superabsorbent (FSA), or the like. The web suitably has a basis weight of at least about 14 gsm (0.4 osy), and particularly at least about 24 gsm (0.7 osy) for improved incorporation and bonding. The fiber denier is desirably less than about 2.0 dpf, and more particularly less than about 1.5 dpf for improved performance. The resulting composite could be treated in process with a topically applied surfactant to enhance the rate of wetting.

In an alternative embodiment, the wet sensation layer 56 comprises a bonded carded web containing at least about 20 weight percent rayon staple fibers, such as from about 20 to about 40 weight percent rayon staple fibers. The rayon fibers may have a denier of at least about 1.5 dpf, and particularly in the range of from about 1.5 dpf to 6 dpf. The bonded carded web desirably has a basis weight of at least about 20 gsm (0.6 osy).

Still alternatively, the wet sensation layer 56 could comprise a polypropylene or polyethylene meltblown web having a durable wettability treatment. Meltblown fibers are typically in the range of 10–30 microns, but can be made larger ("macrofiber meltblown") if a material having greater permeability is desired. The meltblown web may have a basis weight of at least about 50 gsm, and particularly about 150 gsm.

Other suitable materials include patterned point-bonded coform, for example comprising about 40 weight percent polymer and 60 weight percent pulp. A lower polymer content coform could also be employed in combination with a cover material such as for example, a 14 gsm (0.4 osy) treated spunbond of 3.0 dpf fibers.

Die-cut sheets of hydrophilic foam could also be used for the wet sensation layer 56. Suitable foams include cellulose sponges, polyethylene glycol-based polyurethane foams, polyvinyl alcohol-based foams, or the like. Desirably, the foams are reversibly compressible, meaning that they can be compressed into a stable thin layer and then reconstituted into their original foam structures upon addition of liquid.

The support layer 58 may comprise any fabric, such as a nonwoven web or sheet of high wet strength tissue paper, a spunbonded, meltblown or bonded-carded web composed of synthetic polymer filaments, such as polypropylene, polyethylene, polyesters or the like, or a web of natural polymer filaments such as rayon or cotton. The support layer material may optionally be treated with a surfactant to aid in liquid transfer. In particular applications where it may be desirable not to permit urine to flow completely through the pad 50, for example where the pad is to be used with underpants or cloth garments, the support layer 58 may comprise a liquid impermeable material. Suitable liquid impermeable materials would include a web or sheet of plastic film such as polyethylene, polypropylene, polyvinyl chloride or similar material, or a nonwoven, fibrous web which has been suitably constructed and arranged to be substantially liquid impermeable.

The temperature change member 54 desirably includes a temperature change substance 64 that, in the illustrated embodiments, is in the form of particles captured between a pair of containment layers 66. The containment layers 66 form a container to house and limit movement of the temperature change substance 64. The temperature change substance 64 comprises a material which provides a temperature change when placed near the wearer and contacted with urine. The temperature change can be either an absorption or release of heat to change the temperature of the surroundings to a point noticeable to the wearer. An absorption of heat by the temperature change substance 64 will provide the wearer with a cool sensation, while a release of heat by the substance will provide the wearer with a warm sensation.

The temperature change substance 64 is responsive to contact with an aqueous solution such as urine to either absorb or release heat. The mechanism by which this is accomplished is the dissolution of the substance in the aqueous solution, the swelling of the substance in the aqueous solution, or the reaction of the substance in the aqueous solution. In particular embodiments, the temperature change substance 64 is a particle which has a substantial energy difference between a dissolved state and a crystalline state, so that energy in the form of heat is absorbed or released to the environment upon contact with urine. In other embodiments, the temperature change substance 64 releases or absorbs energy during swelling or reacting of the substance in an aqueous solution.

While a wide variety of substances may result in a temperature change when contacted with an aqueous solution, the selection of a particular temperature change substance 64 and the determination of the amount to be used should be based in part on the desired temperature change. Specifically, the training aid 22 desirably provides a surface temperature change when wet of from about 5 to about 25 degrees Fahrenheit (° F.) (2.8°–13.8° C.). To achieve this result, the temperature change substance 64, the amount used, and the location of the substance should be selected so that the possible total energy change is from about 6 to about 30 calories per square centimeter (cal/cm$^2$), which may represent either a possible total energy release of from about 6 to about 30 cal/cm$^2$ or a possible total energy absorption of from about 6 to about 30 cal/cm$^2$. More desirably, the temperature change substance 64, the amount used, and the location of the substance should be selected so that the possible total energy change is from about 12 to about 24 cal/cm$^2$, and more particularly about 18 cal/cm$^2$.

By way of example, urea particles may be selected to provide a cooling sensation, because urea particles absorb heat when dissolved in an aqueous solution. Urea has a heat of solution of approximately −60 calories per gram (cal/g). A desirable add-on amount for the urea particles would be a basis weight of about 0.3 grams per square centimeter (g/cm$^2$). The selection of urea particles at this basis weight results in a possible total energy change of 60 cal/g ×0.3 g/cm$^2$ which equals 18 cal/cm$^2$.

Temperature change substances 64 which absorb or release heat on contact with an aqueous solution desirably have a heat of solution, hydration, or reaction greater than about 40 cal/g or less than about −40 cal/g. The heat of solution, hydration, or reaction is suitably within the range of from about 40 to about 90 cal/g or from about −40 to about −90 cal/g, and more particularly from about 50 to about 64 cal/g or from about −50 to about −64 cal/g, such as urea at −60 cal/g. Suitable basis weights for such temperature change substances 64 range from about 0.1 to about 0.5 g/cm$^2$, and more particularly from about 0.2 to about 0.4 g/cm$^2$.

As referenced above, temperature change substances 64 suitable for use in the training aid 22 include those which dissolve in an aqueous solution. The solubility of such temperature change substances 64 is desirably from about 0.1 to about 3 grams of water (H$_2$O) per gram of material (g/g), and more particularly from about 0.1 to about 2 g/g for improved performance.

Suitable temperature change substances 64 that absorb heat during dissolution can include salt hydrates, such as sodium acetate (H$_2$O), sodium carbonate (10H$_2$O), sodium sulfate (10H$_2$O), sodium thiosulfate (5H$_2$O), and sodium phosphate (10H$_2$O); anhydrous salts, such as ammonium nitrate, potassium nitrate, ammonium chloride, potassium chloride, and sodium nitrate; organic compounds, such as urea, xylitol, and other sugars; or the like. Temperature change substances 64 that release heat during dissolution can include aluminum chloride, aluminum sulfate, potassium aluminum sulfate; or the like. The temperature change substance 64 may also include those substances which absorb or release heat during swelling. By way of illustration, one suitable temperature change particle 64 that releases heat during swelling is a lightly cross-linked partially neutralized polyacrylic acid.

Alternatively, the temperature change substance 64 may include those substances that absorb or release heat upon reaction with an aqueous solution. Examples include ortho esters or ketals such as menthone ketals which result from reacting menthone with alcohols containing 1 to 8 carbons or polyols containing 2 to 8 carbons, and all structural and optical isomers thereof. Particular menthone ketals which may be suitable include menthoneglycerol ketal and menthone-propylene glycol ketal. Particular ketals are disclosed in U.S. Pat. No. 5,348,750 issued Sep. 20, 1994, to Greenberg; and U.S. Pat. No. 5,266,592 issued Nov. 30, 1993, to Grub et al.; which are incorporated herein by reference. While the temperature change substance 64 is best illustrated in the drawings as a particle, it will also be apparent that the temperature change substance may comprise a liquid such as a ketal applied to fibers of a nonwoven web for which the liquid has a high affinity. Such a temperature change substance 64 may be applied by slot coating, printing, a pulsed spray or another suitable technique.

The temperature change substance 64 is desirably although not necessarily in the form of particles sandwiched between the first and second containment layers 66. The first containment layer 66 may, for example, comprise a porous film or fibrous layer. The fibrous layer may comprise a fibrous tissue, a woven or nonwoven fabric, a cellulosic fibrous web, or the like. In one embodiment, for example, the first containment layer 66 can comprise a cellulosic tissue composed of a conventional forming tissue having a basis weight of about 16.6 gsm and manufactured by a continuous wet press (CWP) process from a furnish composed of 100% LL-19 Northern Softwood Kraft (NSWK) fiber. The LL-19 fiber can be obtained from Kimberly-Clark Forest Products, Inc., Terrace Bay, Ontario, Canada. The forming tissue has a Frazier Porosity of about 50–350 cfm/ft$^2$ (cubic-feet-per-minute per square foot).

The second containment layer 66 may, for example, comprise a liquid-permeable web material, such as a liquid-permeable film, tissue, fabric, or the like. The fabric may be woven or nonwoven, and may be composed of a hydrophilic material or composed of a hydrophobic material which has been suitably treated to render it sufficiently hydrophilic. In one embodiment, the second containment layer 66 is composed of a conventional barrier tissue having a basis weight of about 21.2 gsm and manufactured by a CWP machine process from a furnish composed of 50%/50% Hinton EF (Softwood) and LL-16 Northern Hardwood Kraft (NHWK) fiber. The Hinton EF fiber can be obtained from Weldwood, a division of Canada, Ltd., Hinton, Alberta, Canada; and the LL-16 fiber can be obtained from Kimberly-Clark Forest Products, Inc., Terrace Bay, Ontario, Canada. The barrier tissue can have a Frazier Porosity of about 80–120 cfm/ft$^2$.

The training aid 22 is positioned within the training pant 24 so that liquid contacts the temperature change member 54 and the temperature change particles 64 during or shortly after urination. Specifically, the training aid 22 is disposed on the inner surface 40 of the pant 24 in the crotch region 30 or slightly forward of the crotch region. Desirably, the positioning is such that urine introduced into the pant will contact the temperature change member 54, while at the same time being as far forward as possible in regions of the pant 24 that are most likely to be in contact with the wearer. Alternatively, the training aid 22 may be positioned slightly rearward of the crotch region 30 where the pant 24 is also likely to be in contact with the wearer. Positioning the training aid 22 against the wearer allows the temperature change resulting from the particles 64 to be more easily noticed by the wearer.

The temperature change particles 64 are desirably although not necessarily sandwiched between the first and second tissue layers 66. Further, as illustrated in FIGS. 2–3, the temperature change particles 64 are desirably accumulated in a plurality of pockets 68. Without wishing to be bound by any particular theory, positioning the temperature change particles 64 in discrete pockets 68 is thought to enhance performance because the particles in the interior portions of the pockets are, for an extended period of time, damp rather than saturated. As a result, the heat taken in or released by these temperature change particles 64 as they enter solution, swell or react comes from the surrounding environment rather than solely from the urine. Consequently, locating the temperature change particles 64 in pockets 68 within the temperature change member 54 facilitates generation of a cool or a warm sensation in an efficient and cost effective manner.

The illustrated temperature change member 54 may be constructed by routing the first containment layer 66 onto a forming screen in a forming chamber. The forming screen includes a plurality of spaced apart holes. A vacuum of 17 kPa (2.5 psi) is drawn on the forming chamber so that the first containment layer 66 is drawn into the holes in the forming screen to define shallow depressions. The temperature change particles 64 are added to form the pockets 68 of temperature change particles. A brush may be used to evenly distribute the particles 64 into the depressions. A detailed description of an apparatus and process for zoned placement of particulate material is set forth in U.S. patent application Ser. No. 08/274,172 of Heath et al. filed Jul. 12, 1994 (Attorney Docket No. 10,985), which is incorporated herein by reference.

The first and second containment layers 66 may then be secured together by any suitable means such as adhesive bonds, thermal bonds, ultrasonic bonds, stapling, stitching, or the like to sandwich the temperature change particles 64 therebetween. For example, the containment layers 66 may be bonded together by a thin, even or patterned application of construction adhesive applied to the second containment layer 66 before uniting the containment layers 66. The adhesive can be of any suitable type, such as latex adhesive, hotmelt adhesive or the like.

The composite may be pressed together so that any adhesive operably adheres the containment layers 66 together. As a result, the pockets 68 are substantially held and maintained in a desired pattern array composed of individual segregated pockets distributed across the temperature change member 54. The pockets 68 desirably have a diameter of from about 0.5 to 3 cm, and particularly from about 1 to 2 cm, such as about 1.9 cm for improved performance. Additionally, the pockets 68 may be spaced from one another by from about 0.2 to about 10 cm, and particularly from about 0.5 to about 2 cm, such as about 1 cm for improved performance. The basis weight of the temperature change particles 64 within the pockets 68 is suitably from about 0.1 to about 0.5 g/cc, and more particularly from about 0.2 to about 0.4 g/cc.

The composite may be pressed together, by way of example, using an assembly roller having a resilient outer cylindrical surface. The assembly roller outer surface can be constructed with a Shore A-Durometer value of not more than about 60, alternatively not more than about 45, or optionally not more than about 30, and with a Durometer value of not less than about 10, alternatively not less than about 15, and optionally not less than about 20. The assembly roller can be urged against the containment layers 66 with a resilient pressuring means, such as a pneumatic actuator. The pressuring means can be constructed to provide an assembly pressure level of not less than about 5 psi, alternatively not less than about 10 psi, or optionally not less than about 15 psi, and constructed to provide an assembly pressure level of not more than about 300 psi, alternatively not more than about 175 psi, and optionally not more than about 50 psi.

The composite may be trimmed if necessary to provide individual temperature change members 54 of the desired size. The size as well as the shape of the temperature change member 54 is desirably selected in relation to the size and shape of the overall pad 50. By way of example, an individual temperature change member 54 may be rectangular and measure about 4 cm. (1.6 in) by about 7 cm. (2.8 in). The temperature change member 54 suitably contains from about 1 to about 12 grams, and particularly from about 5 about 9 grams, for example about 7 grams, of temperature change particles 64. The temperature change particles 64 are desirably localized in regions having a combined area of from about 1 to about 60 cm$^2$, particularly from about 20 to about 40 cm$^2$, such as about 30 cm$^2$ for improved performance.

The means for attaching the pad 50 to the training pant 24 are provided by an adhesive layer 70 (FIG. 3) and a release strip 72. The adhesive layer 70 is desirably a pressure sensitive adhesive that releasably bonds the casing 52 to the inner surface 40 of the training pant 24. The release strip 72 covers the adhesive layer 70 until the pad 50 is ready to be used, at which time the release strip may be peeled off and discarded. Suitable release strips 72 may be formed of a silicone coated paper and contain printed information, such as instructions for use.

The adhesive layer 70 and the release strip 72 may be smaller than, larger than, or the same size as the casing 52. Desirably, however, the adhesive layer 70 and release strip 72 are the same width as the casing 52 (FIG. 3) and slightly shorter than the length of the casing (FIG. 2). Additionally, the release strip 72 is desirably slightly longer than the longitudinal extent of the adhesive layer 70. In this way, the adhesive attaches the pad 50 to the inner surface 40 over the full width of the pad, but yet the release strip 72 can be easily removed from the casing 52. Alternatively, the release strip 72 may extend beyond the longitudinal ends of the casing 52, such as about 2 cm. (0.75 in) beyond each end.

In one aspect of the invention, the pad 50 desirably allows urine to pass completely through the pad. Thus, the casing 52, including both the wet sensation layer 56 and the support layer 58, and the temperature change member 54 are desirably liquid permeable. For instance, when the release strip 72 is removed and the pad 50 is attached to the inner surface 40 of a training pant 24, liquid applied to the top surface of the pad, which in this embodiment is the wet sensation layer 56, is able to pass completely through the pad to its bottom surface and onto the inner surface of the pant.

To enhance the ability of liquid to pass through the pad 50, the adhesive layer 70 desirably comprises an open pattern of adhesive filaments. The term open pattern is intended to mean that the adhesive filaments are located over the majority of the surface area of the support layer 58 but are spaced from one another so as to not substantially inhibit liquid movement from the pad 50 to the training pant 24. Suitable open patterns of adhesive are illustrated in FIGS. 12A–12E, and include transverse lines, longitudinal lines, parallel swirl patterns, a meltblown pattern, offset parallel lines, or the like.

In another aspect of the invention, urine is able to pass through the pad 50 without the pad retaining a large quantity of liquid. The pad 50 desirably achieves the cool or warm sensation and the wet sensation without providing a significant absorbent capacity. In this regard, the pad 50 desirably has a liquid retention capacity of less than about 6 grams, particularly less than about 5 grams, and more particularly from about 2 to about 3 grams, for improved performance.

One suitable method for determining the liquid retention capacity of a pad 50 is to measure the saturated retention capacity of the pad as follows. The pad or material to be tested, having a moisture content of less than about 7 weight percent, is weighed and submerged in an excess quantity of room temperature (about 23 degrees Celsius) synthetic urine. The pad or material to be tested is allowed to remain submerged for 20 minutes. After 20 minutes, the pad or material is removed from the urine and placed on a Teflon™ coated fiberglass screen having 0.25 inch openings (commercially available from Taconic Plastics Inc., Petersburg, N.Y.) which, in turn, is placed on a vacuum box and covered with a flexible rubber dam material. A vacuum of 3.5 kilopascals (0.5 pounds per square inch) is drawn in the vacuum box for a period of 5 minutes. The pad or material is weighed. The amount of fluid retained by the pad or material being tested is determined by subtracting the dry weight of the pad or material from the wet weight of the pad or material (after application of the vacuum) and is reported as the saturated retention capacity in grams of fluid retained. For relative comparisons, this value can be divided by the weight of the pad or material to give the saturated retention capacity in grams of fluid retained per gram of tested pad or material.

The synthetic urine composition referenced herein comprises 0.31 grams monobasic calcium phosphate monohydrate ($CaH_4(PO_4)_2H_2O$), 0.68 grams monobasic potassium phosphate ($KH_2PO_4$), 0.48 grams magnesium sulphate heptahydrate ($MgSO_4\ 7H_2O$), 1.33 grams potassium sulphate ($K_2SO_4$), 1.24 grams tribasic sodium phosphate dodecahydrate ($Na_3PO_4\ 12H_2O$), 4.4 grams sodium chloride (Nacl), 3.16 grams potassium chloride (KCl), 8.56 grams of urea ($CO(NH_2)_2$), available from BASF-Wyandotte Corporation) and 1 gram methyl paraben and 1 gram Germall 115 preservative (commercially available from Santell Chemical Company, Chicago, Ill.) per liter using distilled water as the solvent. The components are added to 900 milliliters of distilled water in the order given and each dissolved before the next component is added. The solution is finally diluted to one liter.

If material, such as high-absorbency material or fiber is drawn through the fiberglass screen while on the vacuum box, a screen having smaller openings should be used. Alternatively, a piece of tea bag material can be placed between the material and the screen and the final value adjusted for the fluid retained by the tea bag material. Suitable tea bag material is a heat sealable tea bag material grade 542, commercially available from Kimberly-Clark Corporation. The amount of fluid absorbed by the tea bag material is determined by performing the saturated retention capacity test on an empty tea bag. Testing high-absorbency materials or fibers alone can be accomplished using a sealed pouch of tea bag material.

In use, the wearer experiences a cool or warm sensation and a wet feeling during urination. Placement of the pad 50 against the inner surface 40 in the crotch region 30 causes urine to enter the pad 50 during urination. Due to the liquid permeable nature of the pad 50 and the low absorbent capacity of the pad, urine readily passes through the pad and into the training pant 24. As urine passes through the pad 50, urine will come into contact with the temperature change particles 64. Depending on the particular type of particles 64 used in the temperature change member 54, the particles will either absorb or release heat. As a result, the wearer will experience either a cool sensation or a warm sensation upon urination. Additionally, the wet sensation layer 56 retains moisture and thereby produces a wet or damp sensation. The wet sensation layer 56 also improves functioning of the temperature change member 54 by conducting heat between the wearer's skin and the temperature change particles 64.

In terms of the temperature change aspect of the pad 50, the complete pad desirably provides a surface temperature change when wet of from about 5 about 25 degrees Fahrenheit (° F.) (2.8°–13.8° C.). Surface temperature changes within this range are believed to be identifiable to some extent by children of toilet training age. More desirably, the pad 50 provides a surface temperature change when wet of from about 10° to about 20° F. (5.5°–11.1° C.), and particularly about 15° F. (8.3° C.) for improved performance. Also, the cool or warm sensation produced by the temperature change member 54 should last from about 1 to about 120 seconds, and particularly from about 10 to about 60 seconds, such as about 30 seconds.

A suitable procedure for determining the surface temperature change when wet of a product containing a training aid with a temperature change substance is as follows. The test should be conducted in an environment having a stable temperature of 21 to 22 degrees Celsius (70°–72 ° F.) and a stable humidity of about 50 percent. The product to be tested is prepared by removing any elastic side panels and cutting all other elastics to permit the product to lay as flat as possible. The product is positioned in a plexiglass cradle to simulate the configuration of the product in actual use. The center of the product is placed in the deepest portion of the cradle. The training aid should be located 10 cm forward of the center of the product along the product's longitudinal axis.

A liquid dispensing nozzle operatively connected to a liquid dispensing pump is positioned to dispense saline onto the training aid. The tip of the nozzle should be is located 1 cm away from the training aid. The pump is activated to dispense 90 milliliters (ml) of a stabilized isotonic 0.9% saline at a rate of 15 ml/sec. The saline is certified blood bank saline available from The Baxter Healthcare Corporation, Scientific Products Division, McGraw Park, Ill., and is at a temperature of 37 degrees Celsius (98.6 ° F.).

The surface temperature of the training aid at the location of the temperature change substance is measured using a standard thermometer or temperature sensing thermistors connected to a digital display or recording device. The surface temperature 30 seconds after the saline is dispensed is recorded as the test temperature. A reference temperature is obtained by performing this test on a portion of the product not including the training aid or on a similar product without the training aid. The surface temperature change when wet for the training aid is the difference between the test temperature and the reference temperature.

The pad 50 may be generally rectangular as illustrated, or may also be square, oval, hourglass-shaped, T-shaped or irregularly-shaped. To be effective during use, though, the dimensions of the pad 50 should be such that the pad has a surface area of from about 2 to about 70 square centimeters, and desirably from about 10 to about 20 square centimeters for improved performance. Additionally, to fit comfortably within the crotch region 30 of the training pant 24, the pad 50 should also have a longitudinal length dimension of from about 2 to about 30 centimeters, and desirably from about 6 to about 12 centimeters for improved performance, and a transverse width dimension of from about 1 to about 10 centimeters, and desirably from about 2 to about 5 centimeters for improved performance. In one embodiment, the pad 50 has a length dimension of 15 centimeters (6 in.) and a width dimension of 5 centimeters (2 in.). The dimensions of the pad 50 are determined using a ruler with the release strip 72 removed.

Figure 4:
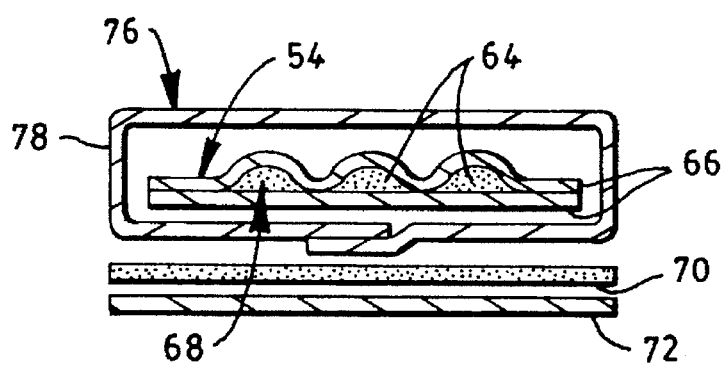
FIG. 4 is a transverse section view similar to FIG. 3, but illustrating an alternative toilet training aid.

An alternative training aid 22 is illustrated by a pad 76 shown in section view in FIG. 4. Components similar to those previously described have been given the same reference numeral. The pad 76 of FIG. 4 is identical to the pad 50 of FIGS. 2 and 3 except that the casing 52 which surrounds the temperature change member 54 consists of a single wrap sheet 78 rather than two separate layers. The single wrap sheet 78 fully wraps the temperature change member 54 and is bonded to itself using adhesives, thermal bonds, ultrasonic bonds, or other suitable means. The wrap sheet 78 may be formed of the same material as the wet sensation layer 56 described above, in which case the pad 76 will produce a wet feeling during use in addition to the cool or warm sensation. Alternatively, the wrap sheet 78 may be formed of the same material as the support layer 58 described above, in which case the pad 76 will produce only a cool or warm feeling during use. In such case, at least the bodyside surface of the wrap sheet 78 would have to be liquid permeable.

Figure 5:
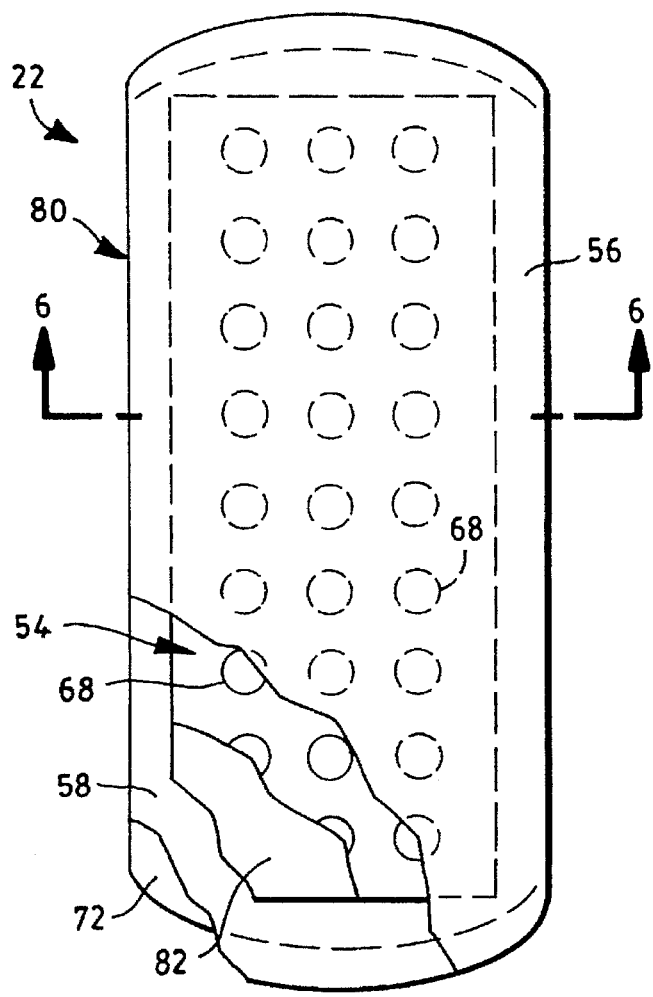
FIG. 5 is a top plan view of an alternative toilet training aid according to the present invention, with portions broken away for purposes of illustration.
Figure 6:
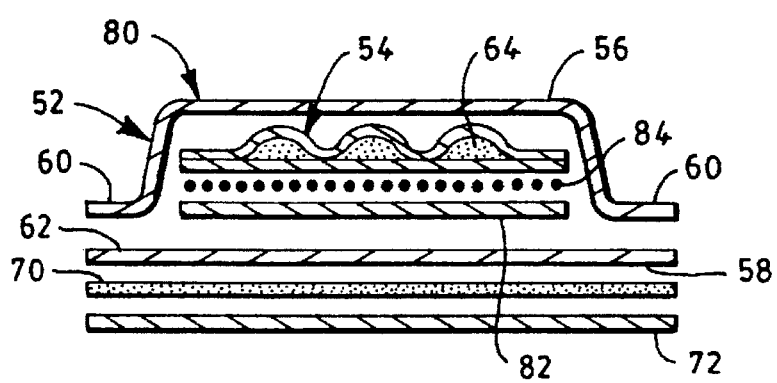
FIG. 6 is a transverse section view taken generally from the plane of the line 6—6 in FIG. 5, but with the components of the toilet training aid separated from one another to better illustrate the invention.

Another embodiment of the toilet training aid 22 is illustrated by a pad 80 shown in FIGS. 5 and 6. The pad 80 is adapted to provide the wearer with a noticeable cool or warm sensation, a wet feeling, and an expanding or contraction dimensional change sensation. The pad 80 includes both a temperature change member 54 and a dimensional change member 82 positioned within a casing 52. The pad 80 also includes an adhesive layer 70 and a release strip 72 for attaching the pad 80 to the training pant 24 or other garment. The illustrated casing 52 includes a wet sensation layer 56 and a support layer 58.

Both the temperature change member 54 and the dimensional change member 82 are desirably sandwiched between the wet sensation layer 56 and the support layer 58. The peripheries 60 and 62 of the wet sensation layer 56 and the support layer 58 may be bonded directly together by adhesives, thermal bonds, ultrasonic bonds, or other suitable means. Additionally, an adhesive layer 84 may optionally be employed to bond the temperature change member 54 and the dimensional change member 82 directly together.

The dimensional change member 82 comprises a material or materials that rapidly undergo a change in at least one dimension when exposed to an aqueous solution. The dimensional change is suitably either an expansion to at least about 2 times a dry dimension or a contraction to less than about one-half (½) of the dry dimension. In particular embodiments, the dimensional change is either an expansion to at least about 5 times the dry dimension or a contraction to less than about one-fifth (⅕) of the dry dimension. For example, the dimensional change member 82 has a wet height dimension that is at least about 5 times greater than its dry height dimension, and more desirably at least about 10 times greater for improved performance. The height dimension of the dimensional change member 82 is perpendicular to the plane formed by the longitudinal and transverse axes of the pad 80 so that the dimensional change is noticeable to the Wearer. The other dimensions, the width and length, of the dimensional change member 82 may remain the same, expand or contract when exposed to an aqueous solution.

In one particular embodiment, the dimensional change member 82 comprises a compressed cellulose sponge having a dry height of about 0.9 mm and a wet height of about 9.5 mm. The height dimensions are measured with the material under a compressive load of 0.2 pounds per square inch.

The noncompressed axes of the material, that is the width and length, expand only about 7 percent from dry to wet states. Additionally, the dimensional change member 82 is desirably generally hydrophobic so that the pad 80 releases liquid to the garment, such as the training pant 24, to which it is attached.

In one aspect of the invention, the dimensional change member 82 is capable of expanding to at least about 5-times its dry height in 10 seconds, and more particularly to at least about 10 times its dry height in 3 second for improved performance. A suitable procedure for determining the time required for an expandable material to reach its maximum dimensional change (previously determined) is to place a sample of expandable material between two screens that are separated by spacers. The spacers are set so that the distance between the two screens is equal to the dimension of the material when it has expanded to its maximum. The expanding material is placed between the screens so that the axis with the maximum expansion is perpendicular to the planes of the two screens. Quickly immerse the screens holding the sample into a volume of distilled water. Start timing when the sample is completely submerged and stop timing when the sample has expanded enough to completely fill the void between the two screens. The time obtained in this procedure is the time to maximum expansion. The procedure can be modified to determine whether a material reaches a particular degree of expansion in a set time, by adjusting the spacing between the screens to the particular degree of interest and noting whether the material contacts both screens by the set time.

Suitable materials for use in the dimensional change member 82 include expandable foams, compressed cellulose sponges, or the like. Particularly desirable expandable foams include those having open, large cell, reticulated structures. Examples of such expandable foams are available from O-Cell-O, General Mills, Inc., Tonawanda, N.Y., USA, and Industrial Commercial Supply Co., Akron, Ohio, USA. The material forming the dimensional change member 82 may be softened by mechanical means or other suitable techniques so as to be less noticeable until urination occurs. One such means that is effective with compressed cellulose sponge is to run the material through a set of meshed gears with the gap between the gears set so that the material is sufficiently scored to make it pliable.

The temperature change member 54 is desirably positioned within the pad 80 so as to be closer to the wearer's skin than the expandable member 82. The temperature change member 54 is desirably positioned between the wet sensation layer 56 and the expandable member 82 so that heat is easily conducted between the wearer's skin and the temperature change substance 64.

In an alternative embodiment, the casing 52 may consist of two separate layers, neither of which function in the same manner as the wet sensation layer 56. In this case the pad 80 would provide a cool or warm sensation, depending upon the type of temperature change substance 64 selected, and an expanding or contracting dimensional sensation, depending upon the type of dimensional change member 82 selected. Still alternatively, the casing 52 may comprise a single wrap sheet 78 as illustrated in FIG. 4, which may be formed of a material like the wet sensation layer 56 or like the support layer 58.

Figure 7:
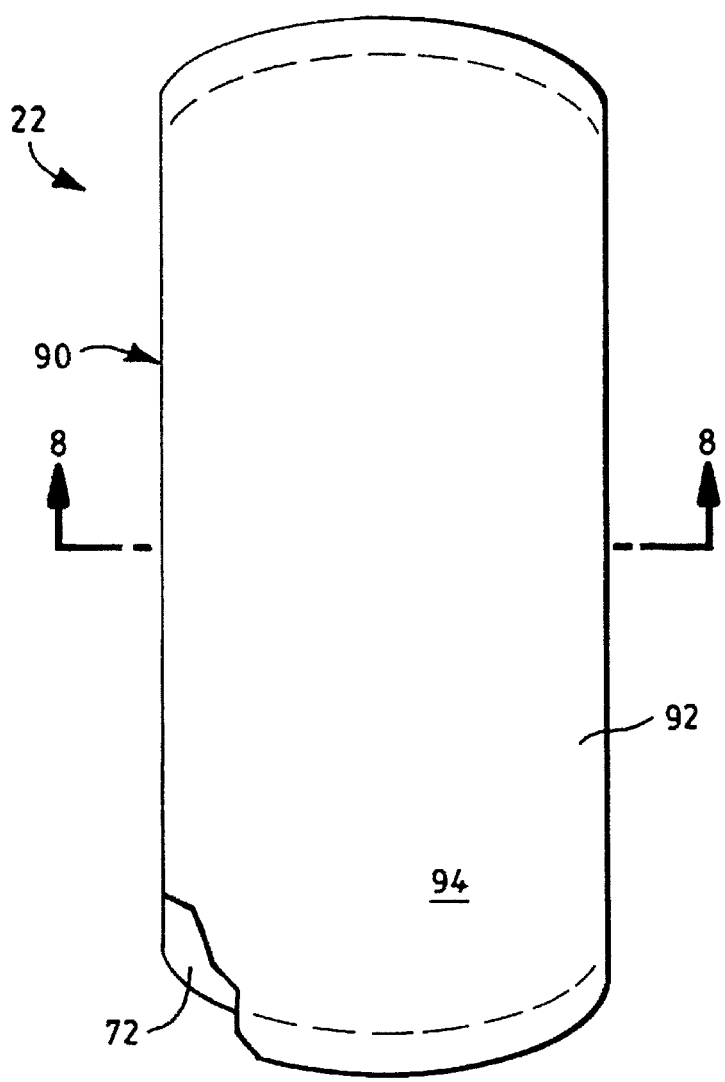
FIG. 7 is a top plan view of an alternative toilet training aid according to the present invention, with portions broken away for purposes of illustration.
Figure 8:
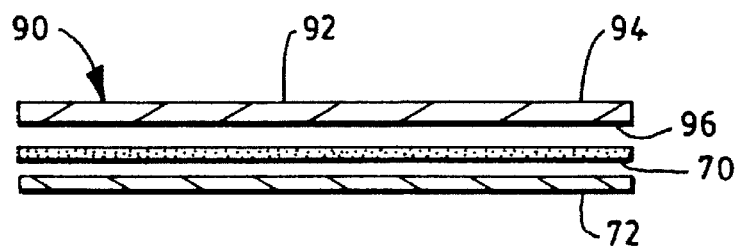
FIG. 8 is a transverse section view taken generally from the plane of the line 8—8 in FIG. 7, but with the components of the toilet training aid separated from one another to better illustrate the invention.

A further embodiment of the toilet training aid 22 is illustrated by a pad 90 shown in FIGS. 7 and 8. The pad 90 includes a body-contacting layer 92, an adhesive layer 70 and a release strip 72. The body-contacting layer 92 has opposite first and second surfaces 94 and 96. The first surface 94 is designed to be positioned against the skin of the wearer during use, and the adhesive layer 70 is applied directly onto the second surface 96. The adhesive layer 70 and the release strip 72 are adapted to attach the pad 90 to a garment such as the illustrated training pant 24 (FIG. 1).

The pad 90 can be adapted to provide the wearer with either a wet sensation or a dimensional change sensation during urination. To provide a wet sensation, the body-contacting layer 92 is formed of a material previously described as a wet sensation layer 56. Alternatively, to provide an expanding or contracting dimensional change sensation, the body-contacting layer 92 is formed of a material previously described as a dimensional change member 82.

In order for the body-contacting layer 92 of the pad 90 to be easily separable from the release strip 72 and remain in a generally flat, unbunched condition during use, the body-contacting layer 92 desirably possesses a certain degree of structural integrity. At the same time, the body-contacting layer 92 cannot be too rigid lest it be uncomfortable and noticeable even in a dry state. Thus, the body-contacting layer desirably has a structural integrity defined in terms of a flexural rigidity of from about 20 to about 40 inch-pounds and more particularly from about 26 to about 30 inch-pounds in the machine direction (MD) of the material, and from about 6 to about 20 inch-pounds and more particularly from about 17 to 18 inch-pounds in the cross direction (CD) of the material for improved performance.

One suitable procedure for measuring the flexural rigidity of the body-contacting layer 92 is a "Stiffness of Cloth, Drape and Flex Test—Cantilever Bending Method" test. This test is intended for determining the drape stiffness (bending length) and flexural rigidity (flex) of fabric by employing the principle of cantilever bending of the fabric under its own weight. This method is not considered suitable for testing knitted cloths or very soft lightweight woven cloths or recommended for cloths When the specimen twists more than 45 degrees.

The test specimens are prepared as follow:

1. The test specimen shall be a rectangular strip of fabric measuring 6.00±0.05 inches (152.4±1.27 mm) long and 1 inch (25.4 mm) wide.
2. Five specimens from each of the warp and filling directions shall be tested from each fabric.
3. The long dimension of the fabric shall be parallel to the warp direction for warp tests and parallel to the filling direction for filling tests. For some material, a longer specimen may be required to obtain a satisfactory reading on the apparatus. The specimen shall be accurately cut from a smooth area of the fabric which has not previously been folded or deformed in any manner. The specimen should be handled as little as possible both before and during the test.

The test uses-the following equipment. Note that one suitable DrapeFlex Stiffness Tester may be purchased from J. J. Press, located in San Diego, Calif., USA.

1. A horizontal platform which is not less than 1 ½ by 6 inches (38.1 by 152.4 mm) in area and has a smooth, low-friction, flat surface such as polished metal or plastic. A leveling bulb or other means for determining that the platform is horizontal before conducting a test shall be incorporated in the platform.
2. An indicator which is positioned against the platform and inclined at an angle of 41 ½ degrees below the plane of the surface of the platform. The indicator should include 2 guide lines not less than 1 ¼ inches (31.75 mm) apart, so that the tip of the specimen can pass between them. It may be formed by the end of a hollow stand on which the horizontal platform is mounted. A rectangular opening in the sloped end of the hollow stand makes it possible to measure fabrics which twist when cut into strips. The length depends on the range of stiffness to be measured. The apparatus may be designed with a longer indicator than is necessary for a 6-inch (152.4 mm) specimen, or an extension may be used.
3. A weight consisting of a metal bar not less than 1 by 6 inches (25.4 by 152.4 mm) in area and about ⅛ inch (3.175 mm) in thickness. In conducting the test, the weight is placed on the specimen so that the leading edges of the specimen and bar coincide and slide out with the specimen.
4. A specimen clamp consisting of a flat metal base plate 1 inch (25.4 mm) wide and approximately 8 inches (203.2 mm) long with a reference line or pointer located 6 inches (152.4 mm) from the leading edge and at right angles to the long dimension, and a flat metal spring for holding the specimen against the base plate. A hand grip for moving the specimen and clamp along the top surface of the horizontal platform may be used.
5. A scale and a pointer for measuring the overhang of the specimen. The scale may be attached to the platform and the pointer to the weight or specimen holder. The scale should be a 6 inch (152.4 mm) scale with 0.1 inch (1 mm) graduation coincident with the leading edge or edge of the indicator when attached to the platform.
6. An analytical or calibrated balance.

The test is performed under standard laboratory conditions in the following manner:

1. The face side of the fabric shall be on the outside of the curvature when tested.
2. The apparatus shall be on a table in such a manner that the platform and inclined reference lines are level and at eye height.
3. When a specimen clamp is used, the specimen shall be placed lengthwise in the clamp with the side up that is to be tested, so that the clamped end of the specimen is exactly even with the reference line on the base of the clamp. With the normal 6 inch specimen, the alignment may alternately be made by adjusting the specimen so that the free end of the specimen and the front end of the clamp coincide. The specimen clamp and specimen shall be placed on the platform so that the reference line on the clamp coincides with the zero point on the scale.
4. When the weight is used, the specimen shall be placed on the platform with the weight on top of it so that the leading edges coincide.
5. The clamp or weight together with the specimen shall be moved slowly and steadily against the ruler or pointer until the bottom of the free edge of the specimen drops to the 41 ½ degree indicator when viewed parallel to the surface of the slope or guide lines. A reading shall be taken from the scale to the nearest 0.05 inch. For a 6-inch specimen this is the overhang of the specimen. For a longer specimen, the length in excess of 6 inches is added to the scale reading to obtain the length of overhang.
6. If the specimen has a slight tendency to twist, the reading shall be taken when the midpoint of the leading edge is at the 41 ½ degree angle.
7. When the 6-inch specimen does not bend sufficiently to permit a reading, a longer specimen shall be used. When the longer specimen is used, it is necessary to increase the length of the indicator sufficiently to accommodate the longer specimen.
8. The specimen shall be weighed to the nearest 0.01 gram on the analytical balance or directly on a calibrated balance.

The test information is calculated as follows:
1. Determine the weight per square yard, W, in ounces per square yard:

$$W = \frac{\text{weight of specimen in gm} \times 36 \text{ in/yd} \times 36 \text{ in/yd}}{\text{area of specimen in sq. in.} \times 28.35 \text{ gms/oz}}$$

2. The drape stiffness (bending length), C, measured in inches, is one-half of the length of the overhang of the specimen when it reaches the 41 ½ degree slope.
3. Flexural rigidity, G, measured in inch-pounds, is calculated as follows:

$$G = C^3 \times W \times 0.482 \times 10^{-4}$$

where:
C=Drape stiffness, in inches.
W=Weight of cloth, in ounces per sq. yd.

The drape or flexural rigidity of the sample shall be the arithmetic average of the results obtained from the specimens tested in each of the warp and filling directions, reported separately. The drape stiffness of the sample shall be reported to the nearest 0.01 inch. The flexural rigidity of the sample shall be reported to the nearest $0.1 \times 10^{-4}$ inch-pound.

In one particular embodiment where the pad 90 provides a wet sensation during urination, the body-contacting layer 92 is formed of a spunbond web comprising side-by-side bicomponent fibers of 40 volume percent HYDROFIL material and 60 volume percent polypropylene. The material desirably has a basis weight of from about 33 to about 40 gsm (1.0–1.2 osy). For lower basis weight materials, an additional tab may be attached to the body-contacting layer 92 in order to facilitate handling. Alternatively, the body-contacting layer 92 may be formed of a spunbond material formed of a thermoplastic polymer available under the tradename HYDROFIL from Allied Corporation. In particular embodiments where the pad 90 provides a bulky sensation during urination, the body-contacting layer 92 is formed of a compressed cellulose sponge.

Figure 9:
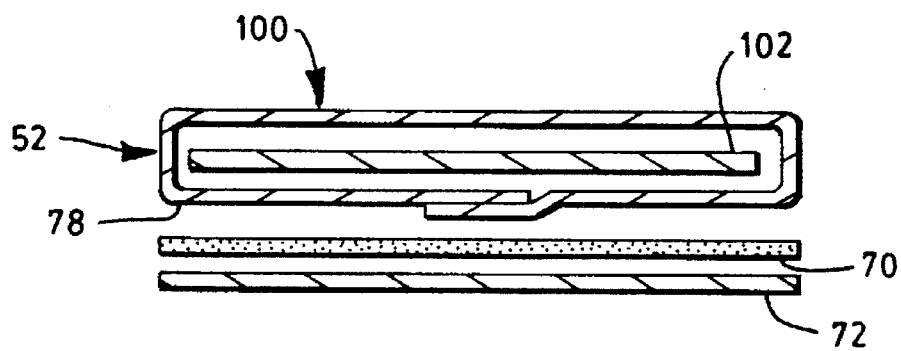
FIG. 9 is a transverse section view similar to FIG. 8, but illustrating an alternative toilet training aid.

Another embodiment of the toilet training aid 22 adapted to provide the wearer with a wet sensation during urination is illustrated by pad 100 in FIG. 9. The pad 100 includes a casing 52, a moisture retaining structure 102, an adhesive layer 70 and a release strip 72. The casing 52 desirably although not necessarily consists of a single wrap sheet 78 that surrounds the moisture retaining structure 102. The single wrap sheet 78 may be bonded to itself using adhesives, thermal bonds, ultrasonic bonds, or other suitable means.

The single wrap sheet 78 in the pad 100 of FIG. 9 is formed of the same material as the wet sensation layer 56 described above. The moisture retaining structure 102 functions to retain a relatively small quantity of liquid, or at least slow down the rate of desorption of all moisture from the pad 100. The wet sensation layer 56 can in this way hold moisture longer and thereby create a prolonged sensation of wetness. This pad 100 is thus particularly well suited for use with a garment that incorporates an absorbent structure, such as a disposable diaper or training pant. By way of example, the moisture retaining structure 102 may comprise a fluff batt of cellulosic material, a coform material comprising cellulosic material and thermoplastic filaments, or the like.

Figure 10:
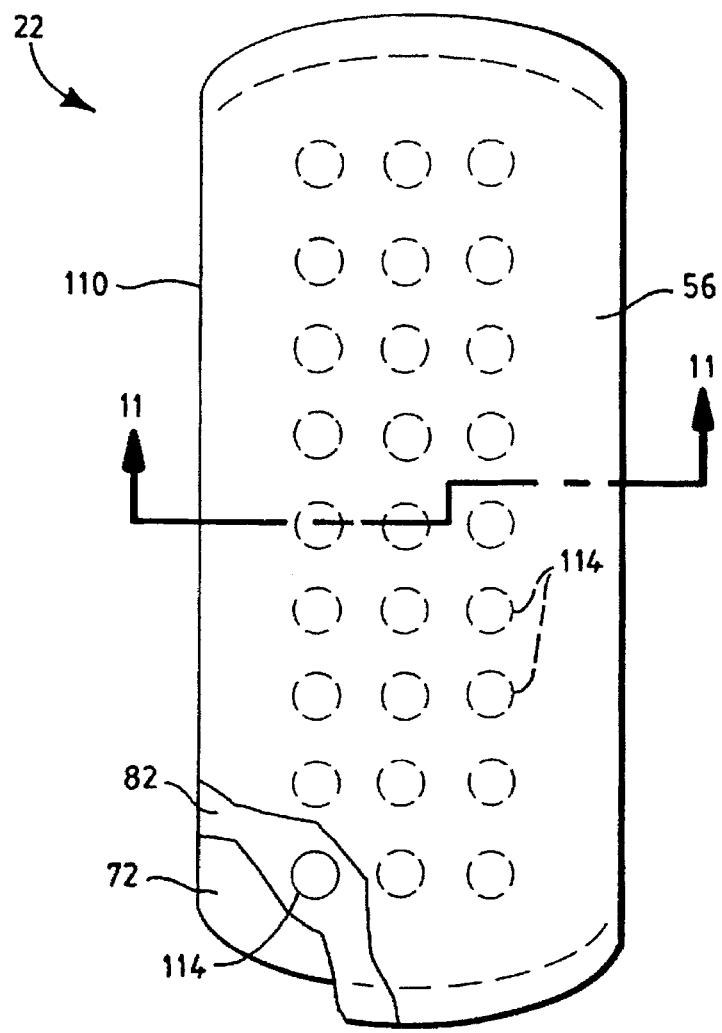
FIG. 10 is a top plan view of an alternative toilet training aid according to the present invention, with portions broken away for purposes of illustration.
Figure 11:
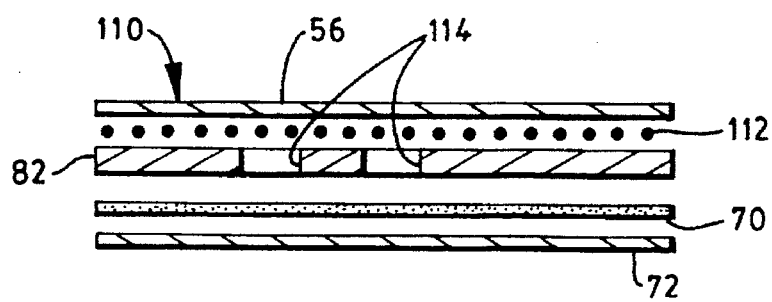
FIG. 11 is a transverse section view taken generally from the plane of the line 11—11 in FIG. 10, but with the components of the toilet training aid separated from one another to better illustrate the invention.
Figure 12A:
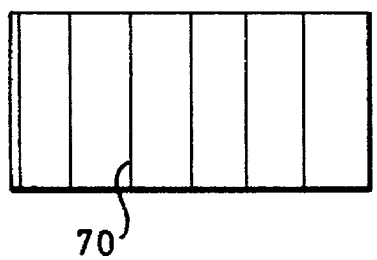
FIGS. 12A, 12B, 12C, 12D and 12E illustrate alternative adhesive patterns for use with toilet training aids.
Figure 12B:
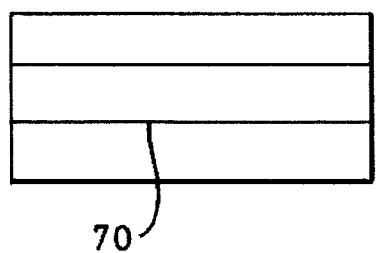
Figure 12C:
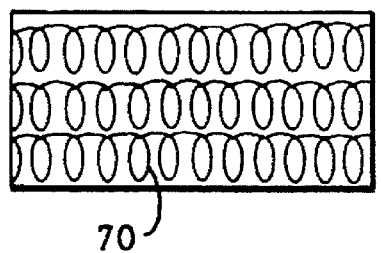
Figure 12D:
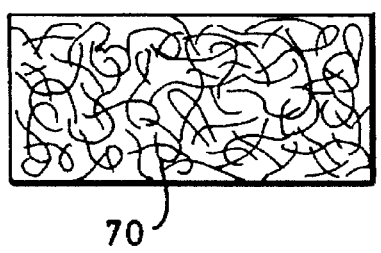
Figure 12E:
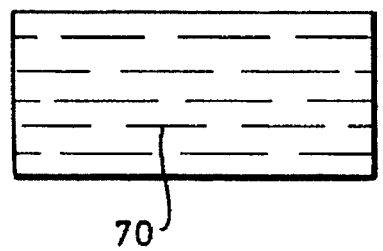

A pad 110 shown in FIGS. 10 and 11 illustrates another embodiment of the toilet training aid 22. The pad 110 is adapted to provide the wearer with a wet and bulky sensation during urination. The pad 110 includes both a wet sensation layer 56 and a dimensional change member 82. A layer of adhesive 112 may be used to bond the wet sensation layer 56 to the dimensional change member 82. Alternatively, the wet sensation layer 56 may be fully wrapped around and bonded to at least the top surface of the dimensional change 82 (not shown). The pad 110 also includes an adhesive layer 70 and a release strip 72 for attaching the pad 110 to a garment.

As illustrated, the dimensional change member 82 includes a plurality of apertures 114 formed therein. While not required, the apertures 114 may further facilitate rapid movement of liquid through the pad 110. It should be noted that such apertures 114 may be employed in the dimensional change members 82 of FIGS. 5–8 as well.

While the training aids 22 may be used with a wide variety of garments, the toilet training process may be particularly successful when the training aids are used with training pants, such as the illustrated disposable training pant 24. Suitable training pants 24 are described in U.S. Pat. 4,639,949 issued Feb. 7, 1987, to Ales et al.; U.S. Pat. No. 4,938,753 issued Jul. 3, 1990, to Van Gompel et al.; U.S. Pat. No. 4,940,464 issued Jul. 10, 1990 to Van Gompel et al.; and U.S. patent application Ser. No. 07/809,993, by Van Gompel et al., filed Dec. 18, 1991, and assigned to the assignee of this application; the disclosures of which are incorporated herein by reference.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. Therefore, the invention should not be limited by the specific embodiments described, but only by the claims.

We claim:

1. A toilet training aid for use with a garment, comprising: a pad comprising:
   a liquid permeable temperature change member comprising a temperature change substance that is adapted to provide a possible total energy change of from about 6 to about 30 cal/cm$^2$; and
   attachment means for attaching the pad to the garment.

2. The toilet training aid of claim 1, wherein the temperature change substance is in the form of particles captured between a pair of containment layers and distributed in a plurality of discrete pockets.

3. The toilet training aid of claim 1, wherein the temperature change substance is in the form of particles selected from the group consisting of sodium acetate (H$_2$O), sodium carbonate (10H$_2$O), sodium sulfate (10H$_2$O), sodium thiosulfate (5H$_2$O), sodium phosphate (10H$_2$O), ammonium nitrate, potassium nitrate, ammonium chloride, potassium chloride, sodium nitrate, urea, and xylitol.

4. The toilet training aid of claim 1, wherein the pad further comprises a casing and the temperature change member is sandwiched within the casing.

5. The toilet training aid of claim 4, wherein:
   the casing comprises a wet sensation layer and a support layer;
   the temperature change member is sandwiched between the wet sensation layer and the support layer.

6. The toilet training aid of claim 5, wherein the support layer comprises a liquid-permeable nonwoven web.

7. The toilet training aid of claim 1, wherein the pad further comprises a wet sensation layer.

8. The toilet training aid of claim 1, wherein the pad has a liquid retention capacity of less than about 6 grams.

9. The toilet training aid of claim 1, wherein the pad has a surface area of from about 2 to about 70 square centimeters.

10. The toilet training aid of claim 1, wherein the pad provides a surface temperature change when wet of from about 5 to about 25 degrees Fahrenheit.

11. The toilet training aid of claim 1, wherein the pad is formed of liquid permeable materials such that liquid can pass through the pad.

12. A toilet training aid for use with a garment, comprising: a pad comprising:

a casing;

a liquid permeable temperature change member within the casing, the temperature change member containing a temperature change substance;

an adhesive layer bonded to the casing; and a release strip releasably attached to the adhesive layer; the pad adapted to provide a surface temperature change when wet of from about 5 to about 25 degrees Fahrenheit.

13. The toilet training aid of claim 12, wherein the casing and the temperature change member comprise liquid permeable materials and the adhesive layer comprises an open pattern of adhesive filaments.

14. The toilet training aid of claim 12, wherein the pad has a liquid retention capacity of less than about 6 grams.

15. The toilet training aid of claim 12, wherein the pad has a surface area of from about 2 to about 70 square centimeters.

16. The toilet training aid of claim 12, wherein the casing comprises a wet sensation layer.

17. The toilet training aid of claim 12, wherein the temperature change substance provides a possible total energy change of from about 6 to about 30 cal/cm$^2$.

18. A toilet training article, comprising:

a three-dimensional training pant having an inner surface; and a toilet training aid comprising a pad attached to the inner surface, the pad comprising a liquid permeable temperature change member that is adapted to provide a possible total energy change of from about 6 to about 30 cal/cm$^2$.

* * * * *